United States Patent [19]
Dieken

[11] Patent Number: 5,852,263
[45] Date of Patent: Dec. 22, 1998

[54] STETHOSCOPE HAVING MICROPHONE IN STEM OF CHESTPIECE

[75] Inventor: Alan P. Dieken, Oakdale, Minn.

[73] Assignee: Minnesota Mining and Manufacturing Company, St. Paul, Minn.

[21] Appl. No.: 455,868

[22] Filed: May 31, 1995

Related U.S. Application Data

[63] Continuation of Ser. No. 976,328, Nov. 13, 1992.

[51] Int. Cl.⁶ .................................................. A61B 7/02
[52] U.S. Cl. .......................................... 181/131; 181/67
[58] Field of Search .................. 181/131, 137; 381/67

[56] References Cited

U.S. PATENT DOCUMENTS

| | | | |
|---|---|---|---|
| 3,087,016 | 4/1963 | Dahl | 381/1 |
| 3,525,810 | 8/1970 | Adler | 381/120 |
| 3,790,712 | 2/1974 | Andries | 381/67 |
| 4,071,694 | 1/1978 | Pfeiffer | 381/67 |
| 4,072,822 | 2/1978 | Yamada | 381/67 |
| 4,200,169 | 4/1980 | MacDonald, III et al. | 181/131 |
| 4,362,164 | 12/1982 | Little et al. | 128/639 |
| 4,440,258 | 4/1984 | Packard | 181/137 |
| 4,458,778 | 7/1984 | Bloom | 181/131 |
| 4,475,619 | 10/1984 | Packard | 181/137 |
| 4,528,690 | 7/1985 | Sedgwick | 381/67 |
| 4,783,813 | 11/1988 | Kempka | 381/67 |
| 4,913,259 | 4/1990 | Packard | 181/131 |
| 5,010,889 | 4/1991 | Bredesen et al. | 128/715 |
| 5,022,405 | 6/1991 | Hü k et al. | 128/715 |
| 5,111,904 | 5/1992 | Packard et al. | 181/131 |
| 5,204,500 | 4/1993 | Dufresne et al. | 181/131 |
| 5,213,108 | 5/1993 | Bredesen et al. | 128/715 |

FOREIGN PATENT DOCUMENTS

| | | | |
|---|---|---|---|
| 0 500 279 A1 | 8/1992 | European Pat. Off. | A61B 7/02 |
| 2 429 585 | 1/1980 | France | A61B 7/04 |
| 91 07 532 | 6/1992 | Germany | H03G 3/02 |

*Primary Examiner*—Howard B. Blankenship
*Attorney, Agent, or Firm*—Gary L. Griswold; John H. Hornickel

[57] ABSTRACT

A stethoscope chestpiece is disclosed having an acoustic-to-electrical transducer residing within the acoustic pathway of the chestpiece. The transducer resides within a mounting that can provide shock attenuation and vibration isolation. The transducer preferably resides within a coaxial position in the acoustic pathway. The chestpiece is useful in a stethoscope which can be electrically connected to auscultation systems.

14 Claims, 3 Drawing Sheets

STETHOSCOPE HAVING MICROPHONE IN STEM OF CHESTPIECE

This is a continuation of application Ser. No. 07/976,328 filed Nov. 13, 1992.

FIELD OF THE INVENTION

The present invention relates generally to stethoscopes and, more particularly, to chestpieces for stethoscopes, especially acoustic stethoscopes having transducers mounted in the chestpiece.

BACKGROUND OF THE INVENTION

Stethoscopes have long been used by physicians to monitor auscultatory sounds. Typically, stethoscopes have been comprised of a chestpiece, a sound transmission mechanism and an earpiece assembly. The chestpiece is adapted to be placed against the skin of a patient for gathering the auscultatory sounds. The sound transmission mechanism acoustically transmits the gathered sound to the earpiece where the physician may monitor the sound.

The chestpiece of conventional acoustic stethoscopes typically is dual sided, top and bottom, to allow either side of the chestpiece to contact the skin of the patient, perhaps for the gathering of auscultatory sounds in different frequency ranges.

The art of auscultation is becoming more sophisticated through the use of electrical or electronic sensors, information processors, and information display. The use of an acoustic stethoscope is a well developed skill that can be enhanced with various forms of electronic amplification, signal processing, and signal display. Two examples of auscultation devices are disclosed in U.S. Pat. No. 5,010,889 (Bredesen et al.) and U.S. Pat. No. 5,213,108 (Bredesen et al.).

Provision for both acoustic and electrical accumulation of sound at a stethoscope chestpiece has been attempted.

U.S. Pat. No. 4,071,694 (Pfeiffer) describes a stethoscope chestpiece which has both an electronic and an acoustic capability. The chestpiece of the stethoscope described therein has a microphone mounted in a location adjacent to the acoustic pathway and is sealed into an internal air channel of the chestpiece.

U.S. Pat. No. 4,362,164 (Little et al.) describes a stethoscope chestpiece where the microphone is positioned in a cavity diametrically opposed to the acoustic pathway.

U.S. Pat. No. 5,204,500 describes an ergonometric stethoscope chestpiece where the microphone is mounted in a pathway different from the acoustic pathway.

SUMMARY OF THE INVENTION

The present invention provides a stethoscope having a chestpiece where the transducer resides within the acoustic pathway in the chestpiece.

The stethoscope chestpiece of the invention comprises a stethoscope housing forming an acoustic pathway and a transducer residing within the acoustic pathway.

The stethoscope of the invention comprises a chestpiece of the invention, a binaural tubing, and an earpiece assembly mechanically connected to provide an acoustic pathway from the chestpiece to the binaural tubing to the earpiece assembly.

Another aspect of the invention preferably provides placing the transducer in a coaxial position within the acoustic pathway in the chestpiece. More preferably, the coaxial position of the transducer is concentrically within the acoustic pathway.

Another aspect of the invention preferably provides placing the transducer in a mounting within the acoustic pathway of the chestpiece in which the mounting has shock attenuating or vibration isolating properties. More preferably, the mounting provides three degrees of freedom of motion of the transducer within chestpiece to minimize ambient sound pickup from vibration or mechanically transferred acoustical energy.

A feature of the invention is the positioning of the transducer within the same stream of sound as is heard by the health care practitioner when using the conventional acoustic stethoscope.

Another feature of the invention is the minimizing of the number of pathways for sound to be received within the chestpiece, thereby minimizing distortion of the acoustic signals.

An advantage of the invention is that the health care practitioner uses the same pathway of sound to receive both acoustically transmitted information and electrically generated information from the stethoscope chestpiece.

The foregoing advantages, construction and operation of the present invention will become more readily apparent from the following description and accompanying drawings.

EMBODIMENTS OF THE INVENTION

Figure 1:
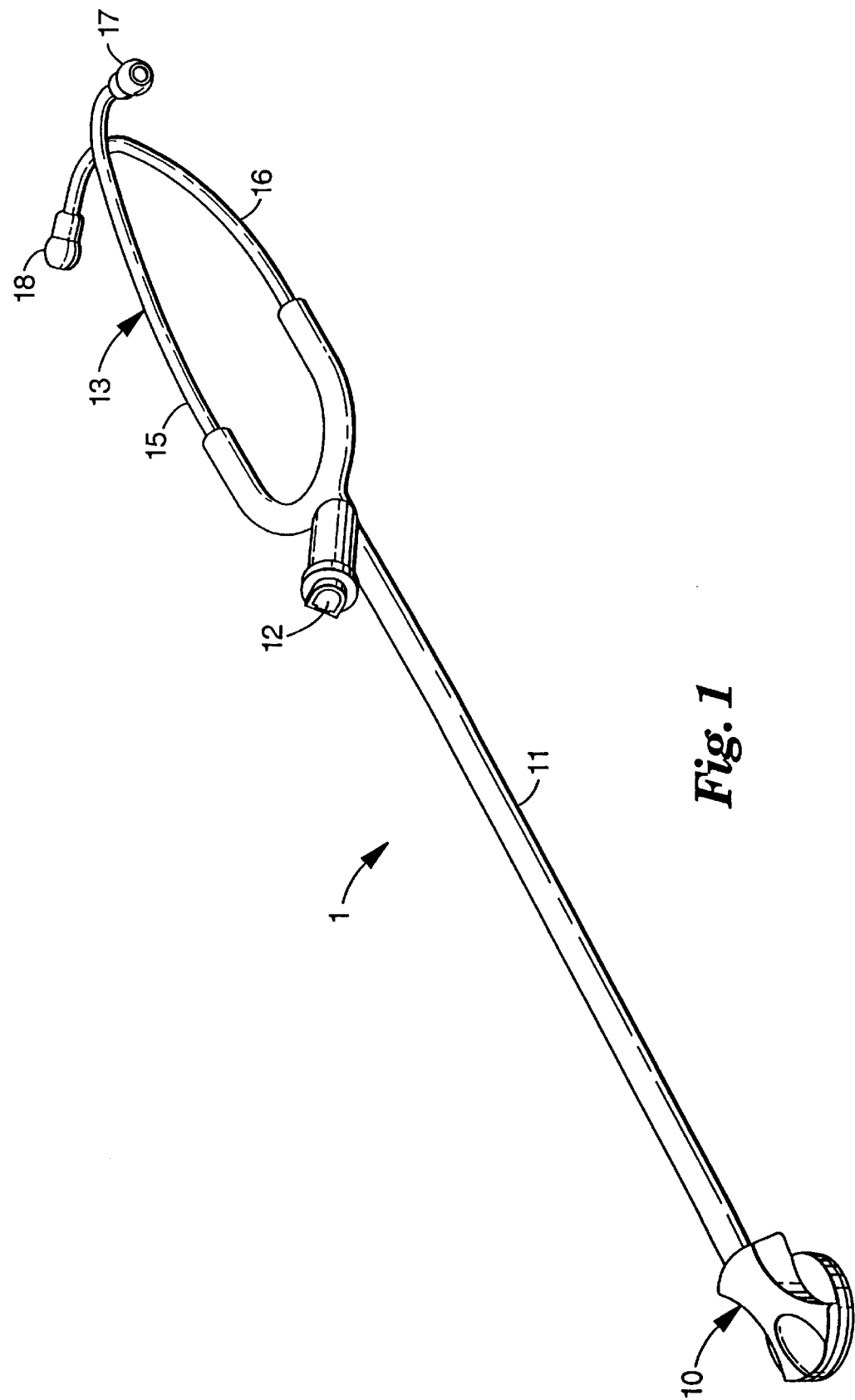
FIG. 1 is a perspective view of a stethoscope incorporating the features of electronic pickup enhancement.

The stethoscope 1 of the present invention illustrated in FIG. 1 has a chestpiece 10 which is easily grasped by the health care practitioner and fits comfortably into the practitioner's hand.

Chestpiece 10 is adapted to receive auscultatory sounds from the body and adapted to transfer such sounds through an acoustic pathway within chestpiece 10 and to binaural tubing 11 which is mechanically and acoustically coupled to an earpiece assembly 13 for contact with the ears of the user. Earpiece assembly 13 has two earpiece tubes 15 and 16 extending from a yoke (not shown) in binaural tubing 11 and adapted to fit in or near the ear of a user. Tubes 15 and 16 terminate in eartips 17 and 18, respectively, for a comfortable fit for the user. Stethoscopes generally are described in U.S. Pat. Nos. 4,200,169 (MacDonald, III et al.); 4,440,258 (Packard); 4,475,969 (Packard); 4,913,259 (Packard et al.); 5,111,904 (Packard et al.); and copending, co-assigned U.S. patent application Ser. No. 07/658,099 (Dieken), the disclosures of which are incorporated by reference herein.

Figure 4:
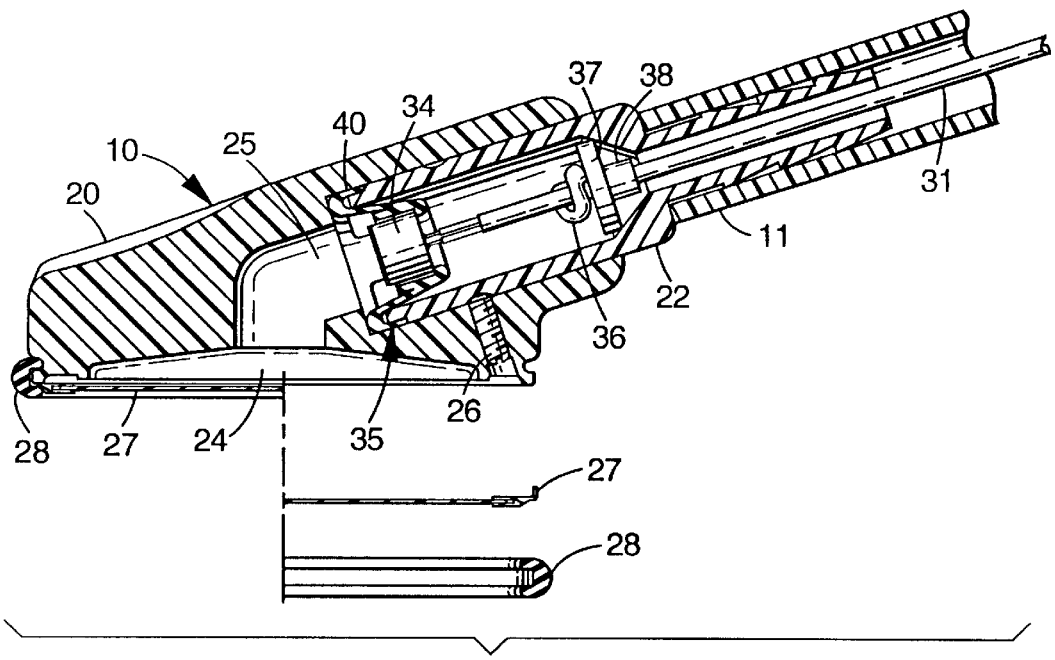
FIG. 4 is a cross-sectional view of the chestpiece and the stem showing the transducer, transducer mounting, and cable strain relief in assembled position.

Within chestpiece 10 is an acoustic to electrical transducer, (as seen in FIG. 4), which is connected to electrical connector 12 by means of an electrical cable (not shown). Electrical connector 12 serves as an electrical link to an auscultation system other than acoustic auscultation, such as those described in U.S. Pat. No. 5,010,889 (Bredesen et al.) and pending U.S. patent application Ser. No. 07/782,079 (Bredesen et al.), the disclosures of which are incorporated by reference.

Figure 2:
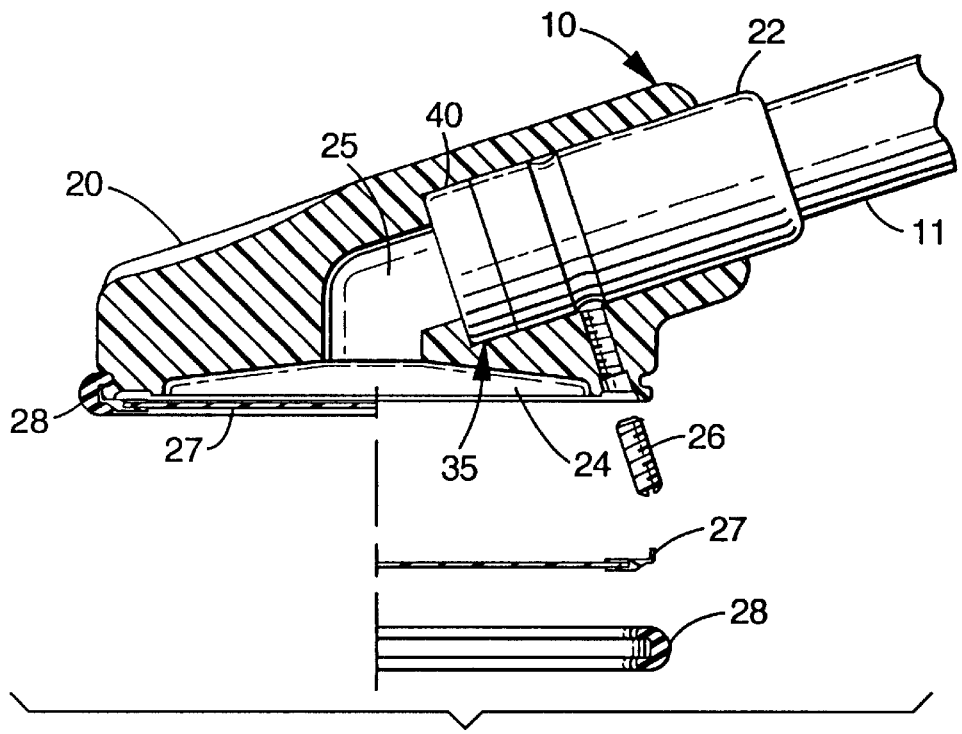
FIG. 2 is a cross-sectional view of the chestpiece incorporating a detachable stem.
Figure 3:
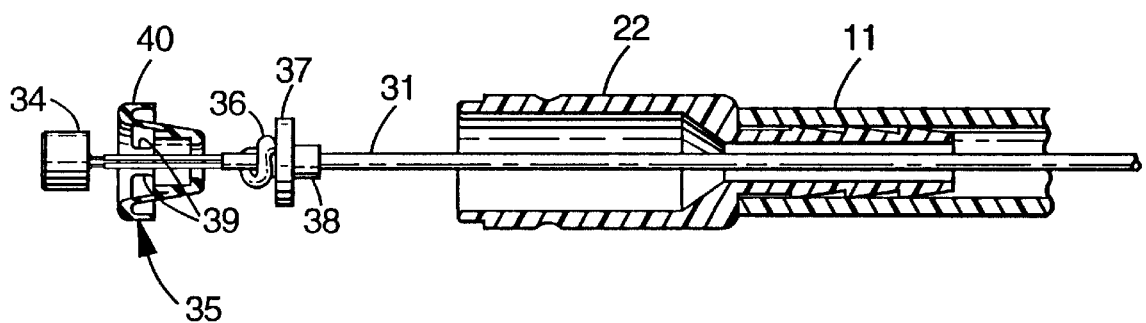
FIG. 3 is a exploded view, in partial cross-section of the stem showing the transducer, transducer mounting, and cable strain relief therein.

The acoustic pathway within chestpiece 10 is shown in FIG. 2. Chestpiece 10 includes a chestpiece housing 20, a stem 22, and a chamber 24 adapted to receive sounds transmitted by a diaphragm 27. An acoustic pathway 25 in the chestpiece proceeds from diaphragm 27 into chamber 24 and into hollow, preferably detachable, stem 22. Diaphragm 27 resides in chestpiece housing 20 in a manner as taught by U.S. Pat. No. 4,475,619 (Packard). If stem 22 is detachable, stem 22 is detachably secured to chestpiece housing 20 by set screw 26 as illustrated in FIG. 4.

Transducer 34 is located within the acoustic pathway 25 of stem 22, communicating electrically with connector 12 through cable 31 comprising wires of about 32 AWG. Preferably, transducer 34 is held within the acoustic pathway 25 using a mounting 35 which has a collar portion 40, preferably adapted to seal environmental sound from entering the acoustic pathway 25 through the interface between stem 22 and chestpiece housing 20.

Cable 31 is physically restrained from placing mechanical force on the transducer 34 by stress relief comprising cable clip 38 secured to the cable 31, a spacer 37 around the cable 31, and a knot 36 in the cable 31. Spacer 37 is interference fit into stem 22. This strain relief and fine gauge wire previously mentioned provide secure positioning of the cable 31, without mechanically stressing the electrical connections, but with minimal mechanical transfer of environmental vibrations to the transducer.

Mounting 35 causes transducer 34 to be positioned, preferably coaxially, within the same acoustic pathway 25 as employed for acoustic auscultation through binaural tube 11 to the user and for the transducer to receive unobstructed contact with the stream of sound that is also heard by the user. More preferably, the transducer is concentrically positioned within the acoustic pathway 25. At least one opening 39 resides in mounting 35 in location(s) around transducer 34 permit passage of sound in the pathway 25 past transducer 34 and into the remainder of stem 22 and thence to binaural tube 11 and to the ears of the user.

Mounting 35 can be made from a range of elastomeric materials to provide flexibility for the positioning of transducer 34 in the acoustic pathway 25. Such flexibility can provide the very desirable advantage of shock attenuation or other vibration isolation for the transducer 34 within the stethoscope chestpiece 10.

Preferably, mounting 35 is molded from silicone rubber molding material having a Shore A durometer of about 20–50, and preferably about 40 Shore A. The durometer scale of hardness-softness is defined by the Shore system of measurement and adopted as ASTM Standard D2240. Such rubber material is commercially available from General Electric Company, Schenectady NY.

Transducer 34 can be any transducer which is capable receiving sound waves and changing such waves into electrical signals. Nonlimiting examples include pressure transducers and microphones. Presently preferred for transducer 34 is Panasonic model WM-063Y microphone from Panasonic of Secaucus, N.J.

Figure 5:
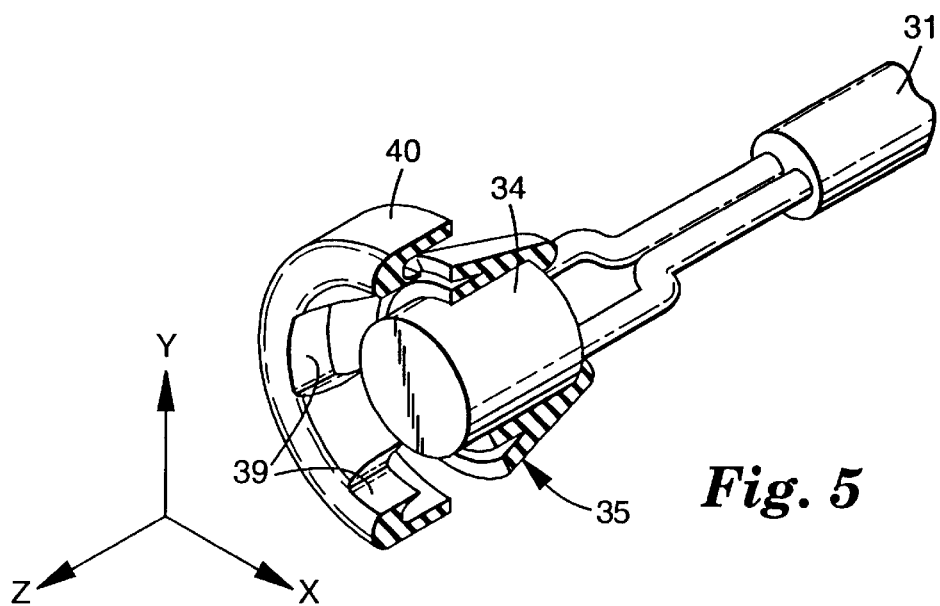
FIG. 5 is a partial cross-section of the transducer and transducer mounting in spatial orientation.

The flexible positioning of transducer 34 within acoustic pathway 25 using mounting 35 of elastomeric material minimizes the conversion of extraneous sound into electrical signals by the transducer 34. Vibration or environmental sound can be introduced to a chestpiece in all spatial directions. Three degrees of freedom of motion for transducer 34 within mounting 35 are illustrated in FIG. 5. Isolation through constrained motion in each of the X, Y, and Z directions is controlled by the configuration of the mounting 35 as shown in FIG. 5 and the use of a flexible material for mounting 35. This flexibility of mounting 35 in three orthogonal directions attenuates shock and other sound-inducing vibrations, thereby isolating, to the maximum extent possible, the transducer 34 from all sounds other than the sound passing within the acoustic pathway 25.

While the embodiments of the invention have been described, the invention is not limited thereto. The claims of the invention follow.

What is claimed is:

1. A stethoscope chestpiece capable of transmitting auscultatory sounds both acoustically and electrically, comprising:

(a) a stethoscope housing having a stem and forming an acoustic pathway for acoustic auscultation;

(b) a mounting in the stem (c) a cable mounted within the acoustic pathway that is capable of transmitting electrically generated information: and (d) an acoustic to electrical transducer within the mounting in the stem of the chestpiece, wherein the transducer is electrically connected to the cable, and wherein the transducer is positioned within the same acoustic pathway as employed for acoustic auscultation.

2. The chestpiece according to claim 1, wherein the transducer resides coaxially within the acoustic pathway.

3. The chestpiece according to claim 1, wherein the mounting comprises an elastomeric material.

4. The chestpiece according to claim 3, wherein the mounting has at least one opening to permit passage of sound in the acoustic pathway.

5. The chestpiece according to claim 3, wherein the mounting is flexible in three orthogonal directions to attenuate shock and other sound-inducing vibrations.

6. The chestpiece according to claim 5, wherein the stem is detachable from the housing, and wherein the mounting further comprises a collar portion engaging the detachable stem and the stethoscope housing, whereby a seal from environmental sound is provided.

7. The chestpiece according to claim 5, wherein the mounting positions the transducer concentrically within the acoustic pathway and wherein the transducer is a microphone.

8. A stethoscope comprising:

(a) a chestpiece, (b) a binaural tubing mechanically connected to the chestpiece, and (c) an earpiece assembly mechanically connected to the binaural tubing to provide an acoustic pathway from the chestpiece to the binaural tubing to the earpiece assembly, wherein the chestpiece comprises (1) a stethoscope housing having a stem and forming an acoustic pathway for acoustic auscultation;

(2) a mounting in the stem (3) a cable mounted within the acoustic pathway that is capable of transmitting electrically generated information; and (4) an acoustic to electrical transducer within the mounting in the stem of the chestpiece, wherein the transducer is electrically connected to the cable, and wherein the transducer is positioned within the same acoustic pathway as employed for acoustic auscultation.

9. The stethoscope according to claim 8, wherein the transducer resides coaxially within the acoustic pathway.

10. The stethoscope according to claim 8, wherein the mounting comprises an elastomeric material.

11. The stethoscope according to claim 10, wherein the mounting has at least one opening to permit passage of sound in the acoustic pathway.

12. The stethoscope according to claim 10, wherein the mounting is flexible in three orthogonal directions to attenuate shock and other sound-inducing vibrations.

13. The stethoscope according to claim 12, wherein the stem is detachable from the housing, and wherein the mounting further comprises a collar portion engaging the detachable stem and the stethoscope housing, whereby a seal from environmental sound is provided.

14. The stethoscope according to claim 12, wherein the mounting positions the transducer concentrically within the acoustic pathway and wherein the transducer is a microphone.

\* \* \* \* \*